US00PP17414P2

(12) United States Plant Patent
Oliver

(10) Patent No.: US PP17,414 P2
(45) Date of Patent: Feb. 13, 2007

(54) ***HEUCHERA* PLANT NAMED 'ROSE MAJESTY'**

(50) Latin Name: *Heuchera×hybrida*
Varietal Denomination: Rose Majesty

(76) Inventor: Charles Oliver, 921 Scottdale-Dawson Rd., Scottdale, PA (US) 15683

( * ) Notice: Subject to any disclaimer, the term of this patent is extended or adjusted under 35 U.S.C. 154(b) by 20 days.

(21) Appl. No.: 11/151,889

(22) Filed: Jun. 14, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Heuchera* plant named 'Rose Majesty', characterized by its full, densely foliated and uniformly mounded plant habit; purple bronze and slightly silver-colored foliage; numerous large pink-colored flowers arranged on mostly erect panicles; and excellent garden performance.

1 Drawing Sheet

Botanical designation: *Heuchera×hybrida.*
Cultivar denomination: 'Rose Majesty'.

BACKGROUND OF THE INVENTION

The present invention relates to a new and distinct cultivar of *Heuchera* plant, botanically known as *Heuchera×hybrida* and hereinafter referred to by the name 'Rose Majesty'.

The new *Heuchera* is a product of a planned breeding program conducted by the Inventor in Scottdale, Pa. The objective of the breeding program is to create new *Heuchera* cultivars having good plant vigor, dense and uniform plant habit, and showy and attractive flower and leaf coloration.

The new *Heuchera* was discovered by the Inventor in a controlled environment in Scottdale, Pa., from seedling progeny from a cross-pollination made by the Inventor in May, 2000, of a proprietary selection of *Heuchera×hybrida* identified as code number H99-6A, not patented, as the female, or seed, parent with a proprietary selection of *Heuchera×hybrida* identified as code number H99-9B, not patented, as the male, or pollen, parent. The new *Heuchera* was selected by the Inventor in June, 2002. The selection of this plant was based on its desirable flower and foliage coloration.

Asexual reproduction of the new *Heuchera* by cuttings in a controlled environment in Scottdale, Pa., since October, 2002, has shown that the unique features of this new *Heuchera* are stable and reproduced true to type in successive generations.

SUMMARY OF THE INVENTION

The cultivar Rose Majesty has not been observed under all possible environmental conditions. The phenotype may vary somewhat with variations in environment such as temperature and light intensity, without, however, any variance in genotype.

The following traits have been repeatedly observed and are determined to be the unique characteristics of 'Rose Majesty'. These characteristics in combination distinguish 'Rose Majesty' as a new and distinct cultivar of *Heuchera:*

1. Full, densely foliated and uniformly mounded plant habit.
2. Purple bronze and slightly silver-colored foliage.
3. Numerous large pink-colored flowers arranged on mostly erect panicles.
4. Excellent garden performance.

Plants of the new *Heuchera* can be compared to plants of the female parent, the proprietary *Heuchera* selection identified as H99-6A. In side-by-side comparisons conducted by the Inventor in Scottdale, Pa., plants of the new *Heuchera* differed from plants of the female parent selection in the following characteristics:

1. Plants of the new *Heuchera* had larger leaves than plants of the female parent selection.
2. Plants of the new *Heuchera* and the female parent selection differed in leaf coloration.
3. Plants of the new *Heuchera* had taller inflorescences than plants of the female parent selection.
4. Plants of the new *Heuchera* and the female parent selection differed in flower coloration.

Plants of the new *Heuchera* can be compared to plants of the male parent, the proprietary *Heuchera* selection identified as code number H99-9B. In side-by-side comparisons conducted by the Inventor in Scottdale, Pa., plants of the new *Heuchera* differed from plants of the male parent selection in the following characteristics:

1. Plants of the new *Heuchera* and the male parent selection differed in leaf coloration
2. Plants of the new *Heuchera* had taller inflorescences than plants of the male parent selection.
3. Plants of the new *Heuchera* had smaller flowers than plants of the male parent selection.
4. Plants of the new *Heuchera* and the male parent selection differed in flower coloration.

Plants of the new *Heuchera* can be compared to plants of the cultivar Harmonic Convergence, disclosed in U.S. Plant Pat. No. 11,111. In side-by-side comparisons conducted by the Inventor in Scottdale, Pa., plants of the new *Heuchera* differed from plants of the cultivar Harmonic Convergence in the following characteristics:

1. Plants of the new *Heuchera* had longer leaf petioles than plants of the cultivar Harmonic Convergence.
2. Plants of the new *Heuchera* had non-basally branching inflorescences whereas plants of the cultivar Harmonic Convergence had basally branching inflorescences.
3. Plants of the new *Heuchera* had more flowers per inflorescence than plants of the cultivar Harmonic Convergence.
4. Plants of the new *Heuchera* had larger flowers than plants of the cultivar Harmonic Convergence.
5. Plants of the new *Heuchera* and the cultivar Harmonic Convergence differed in flower form and coloration.

BRIEF DESCRIPTION OF THE PHOTOGRAPH

The accompanying colored photograph illustrates the overall appearance of the new *Heuchera,* showing the colors as true as it is reasonably possible to obtain in colored reproductions of this type. Colors in the photograph may differ slightly from the color values cited in the detailed botanical description which accurately describe the colors of the new *Heuchera.* The photograph comprises a side perspective view of a typical flowering plant of 'Rose Majesty'.

DETAILED BOTANICAL DESCRIPTION

In the following description, color references are made to The Royal Horticultural Society Colour Chart, 1995 Edition, except where general terms of ordinary dictionary significance are used. The aforementioned photograph and following detailed botanical description describe plants grown in Scottdale, Pa. in a glass-covered greenhouse and under cultural conditions which approximate commercial practice. Plants were grown as single plants in one-gallon containers and were about one year old when the photograph and description were taken. During the production of the plants, day temperatures ranged from 15 to 26° C. and night temperatures ranged from 5 to 15° C.

Botanical classification: *Heuchera×hybrida* cultivar Rose Majesty.

Parentage:

*Female, or seed, parent.*—Proprietary selection of *Heuchera×hybrida* identified as code number H99-6A, not patented.

*Male, or pollen, parent.*—Proprietary selection of *Heuchera×hybrida* identified as code number H99-9B, not patented.

Propagation:

*Type.*—By cuttings.

*Time to initiate roots.*—Summer: About 15 days at 23° C. Winter: About 21 days at 17° C.

*Time to produce a rooted cutting.*—Summer: About 45 days at 23° C. Winter: About 60 days at 17° C.

*Root description.*—Fine, fibrous; white in color.

*Rooting habit.*—Freely branching.

Plant description:

*Appearance.*—Perennial; basal rosette plant habit with leaves developing from the base; densely foliated; full, mounded and uniform plant habit with upright panicles with pink-colored flowers. Vigorous growth habit.

*Plant size.*—Height, soil level to top of foliar plane: About 10 cm. Height, soil level to top of panicles: About 65 cm. Diameter or spread: About 30 cm.

*Foliage description.*—Arrangement: Basal rosette, simple. Length: About 9 to 12 cm. Width: About 9 to 12 cm. Shape: Rounded cordate, seven-lobed. Apex: Broadly obtuse, lobed. Base: Auriculate. Margin: Crenate with ciliation. Texture, upper and lower surfaces: Slightly pubescent; slightly rough. Venation pattern: Palmate, reticulate. Color: Developing and fully expanded leaves, upper surface: 198A; venation, 189A underlain with 187A. Developing and fully expanded leaves, lower surface: 187A; venation, 187A. Petiole: Length: About 8 to 10 cm. Diameter: About 2 mm. Texture, upper and lower surfaces: Smooth. Color, upper and lower surfaces: 187B.

Flower description:

*Appearance/arrangement.*—Single campanulate flowers arranged on loose, narrow and mostly erect panicles; about ten to twelve panicles develop during the flowering season each panicle with about 100 to 150 flowers and flower buds. Flowers face mostly outward to slightly downward. Flowering continuous. Flowers persistent. Flowers not fragrant.

*Time of flowering.*—Plants May through August in Scottdale, Pa.; flowering continuous during this period.

*Inflorescence longevity.*—Individual inflorescences last about one week on the plant.

*Inflorescence size.*—Length: About 50 to 65 cm. Diameter: About 6 cm.

*Flower size.*—Diameter: About 5 mm. Depth (height): About 8 mm.

*Flower buds.*—Height: About 5 mm. Diameter: About 3 mm. Shape: Bulbous. Color, at stage of showing color: 59B.

*Sepals.*—Quantity/arrangement: Five sepals; radially symmetrical and fused at base. Calyx length: About 7 mm. Calyx diameter: About 5 mm. Shape: Elongate. Apex: Obtuse. Margin: Entire. Texture, upper and lower surfaces: Pubescent. Color, upper surface: Close to 155D underlain with 59D. Color, lower surface: 59D; central band, close to 155D, shaded with 59D.

*Petals.*—Quantity/arrangement: Five minute petals; radially symmetrical. Length: About 3.5 mm. Width: About 1 mm. Shape: Spatulate. Apex: Acute. Margin: Serrate. Texture, upper and lower surfaces: Smooth. Color, upper and lower surfaces: Close to 155D.

*Flower bracts.*—Length: About 3 mm. Width: About 1 mm. Shape: Lanceolate. Apex: Acute. Margin: Serrate. Texture, upper and lower surfaces: Pubescent. Color, upper and lower surfaces: 187B.

*Peduncle.*—Strength: Strong. Aspect: Erect to about 30° from vertical. Length: About 32 to 40 cm. Diameter: About 2.2 mm. Texture: Smooth. Color: 187B.

*Pedicels.*—Strength: Strong. Aspect: About 30° from vertical. Length: About 0.8 mm. Diameter: About 0.2 mm. Texture: Pubescent. Color: 187B.

*Reproductive organs.*—Androecium: Stamen number: Five per flower. Anther shape: Oval. Anther length: About 1 mm. Anther width: About 0.6 mm. Anther color: 24A. Amount of pollen: Moderate. Pollen color: 24A. Gynoecium: Pistil number: Two per flower. Pistil length: About 6 mm. Stigma shape: Round. Stigma color: 157A. Style length: About 4 mm. Style color: 157A. Ovary color: 157A.

*Seed.*—Size: About 0.3 mm by 0.6 mm. Color: Close to 202A.

Disease/pest resistance: Resistance to pathogens and pests common to *Heuchera* has not been observed on plants grown under commercial conditions.

Weather/temperature tolerance: Plants of the new *Heuchera* have been observed to have excellent garden performance. Plants of the new *Heuchera* have demonstrated good tolerance to rain, wind, night temperatures as low as −35° C., and day temperatures as high as 45° C.

It is claimed:

1. A new and distinct cultivar of *Heuchera* plant named 'Rose Majesty', as illustrated and described.

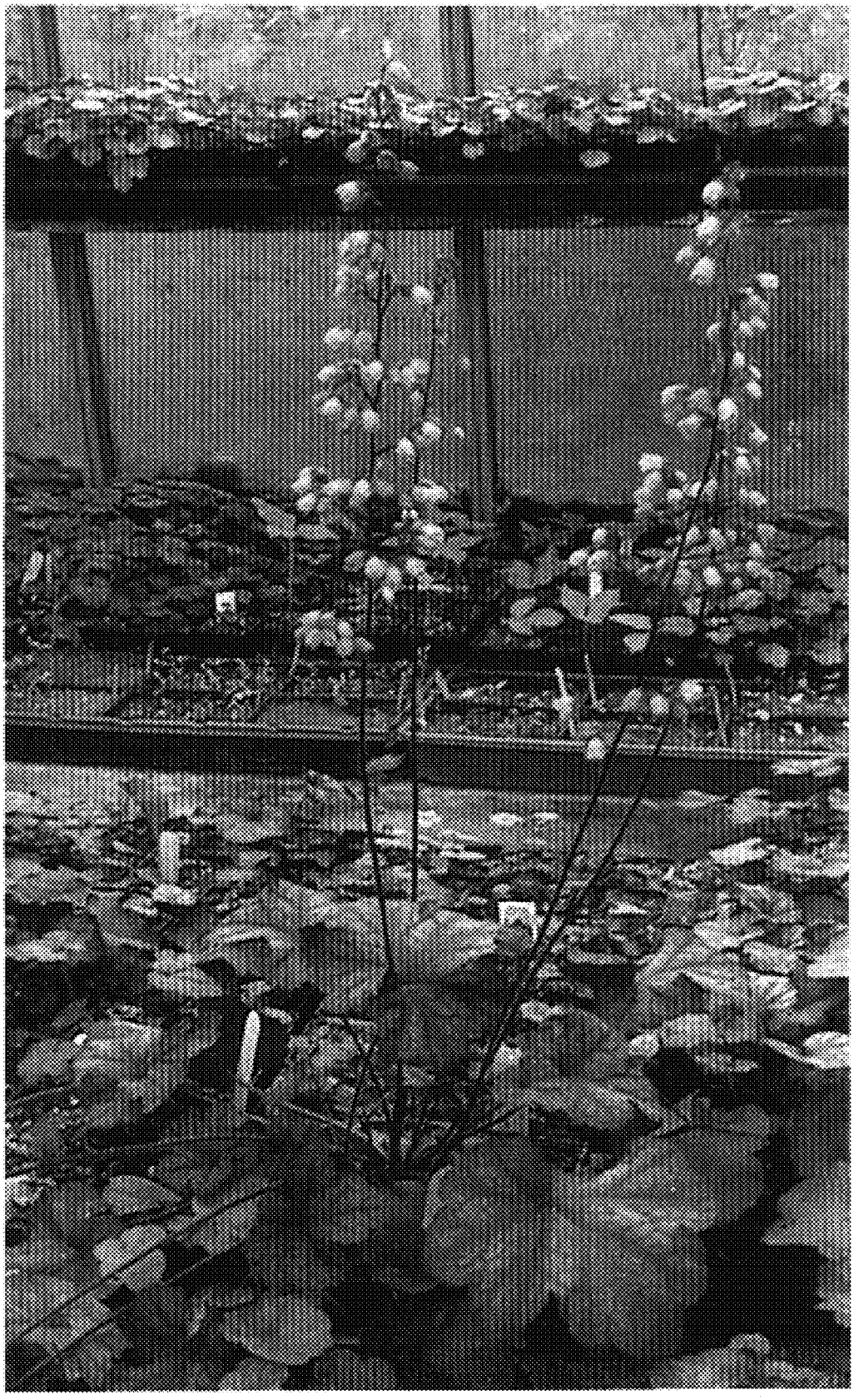

* * * * *